United States Patent
Meilland

(10) Patent No.: US 11,917,978 B2
(45) Date of Patent: *Mar. 5, 2024

(54) MINIATURE ROSE PLANT NAMED 'MEIBENBINO'

(71) Applicant: THE CONARD PYLE COMPANY, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/676,522

(22) Filed: Feb. 21, 2022

(65) Prior Publication Data

US 2022/0248628 A1 Aug. 11, 2022

Related U.S. Application Data

(63) Continuation-in-part of application No. 16/544,290, filed on Aug. 19, 2019, now Pat. No. 11,252,928, which is a continuation-in-part of application No. 15/932,925, filed on May 23, 2018, now Pat. No. Plant 30,811.

(30) Foreign Application Priority Data

Sep. 21, 2017 (QZ) .................................. 2017/2341

(51) Int. Cl.
*A01H 5/02* (2018.01)
*A01H 6/74* (2018.01)

(52) U.S. Cl.
CPC .............. *A01H 6/749* (2018.05); *A01H 5/02* (2013.01)

(58) Field of Classification Search
CPC .................................. A01H 6/749; A01H 5/02
USPC .......................................... Plt./122; 800/323
See application file for complete search history.

(56) References Cited

U.S. PATENT DOCUMENTS

| | | |
|---|---|---|
| PP5,608 P | 12/1985 | Winchel |
| 5,034,323 A | 7/1991 | Jorgensen et al. |
| 5,107,065 A | 4/1992 | Shewmaker et al. |
| 5,453,566 A | 9/1995 | Shewmaker et al. |
| 5,463,175 A | 10/1995 | Barry et al. |
| 5,500,365 A | 3/1996 | Fischhoff et al. |
| 5,633,435 A | 5/1997 | Barry et al. |
| 5,689,052 A | 11/1997 | Brown et al. |
| 5,759,829 A | 6/1998 | Shewmaker et al. |
| 5,880,275 A | 3/1999 | Fischhoff et al. |
| 6,423,885 B1 | 7/2002 | Waterhouse et al. |
| 6,453,242 B1 | 9/2002 | Eisenberg et al. |
| 6,528,700 B1 | 3/2003 | Baszczynski et al. |
| 6,753,139 B1 | 6/2004 | Baulcombe et al. |
| 6,785,613 B2 | 8/2004 | Eisenberg et al. |
| 6,911,575 B1 | 6/2005 | Baszczynski et al. |
| PP16,739 P3 | 6/2006 | Meilland |
| 7,138,565 B2 | 11/2006 | Waterhouse et al. |
| 7,151,201 B2 | 12/2006 | Barbas, III et al. |
| 7,177,766 B2 | 2/2007 | Eisenberg et al. |
| PP17,877 P3 | 7/2007 | Meilland |
| 7,713,715 B2 | 5/2010 | Speer et al. |
| 7,788,044 B2 | 8/2010 | Eisenberg et al. |
| PP21,612 P2 * | 1/2011 | Meilland .................. A01H 5/00 Plt./107 |
| 9,930,811 B2 | 3/2018 | Noteboom |
| PP30,383 P3 | 4/2019 | Farrow |
| 2005/0289675 P1 | 12/2005 | Radler |
| 2007/0300332 P1 | 12/2007 | Cockcroft |
| 2010/0076057 A1 | 3/2010 | Sontheimer et al. |
| 2014/0179006 A1 | 6/2014 | Zhang |
| 2014/0294773 A1 | 10/2014 | Brouns et al. |

FOREIGN PATENT DOCUMENTS

WO 2014068346 A2 5/2014

OTHER PUBLICATIONS

Poehlman et al. Breeding Field Crops, Fourth Edition, Chapter 6, pp. 106-115 (Year: 1995).*
Pohlman et al. Breeding Field Crops, Fourth Edition, Chapter 3, pp. 38-59 (Year: 1995).*
Aukerman, M. et al., Regulation of Flowering Time and Floral Organ Identity by a MicroRNA and Its APETALA2-Like Target Genes, 15 The Plant Cell 2730-2741 (2003).
Barrangou, R. et al., CRISPR Provides Acquired Resistance Against Viruses in Prokaryotes, 315 Science Magazine 1709-1712 (2007).
Baulcombe, D.C., Fast forward genetics based on virus-induced gene silencing, 2(2) Curr Opin Plant Biol. 109-113 (1999) (Abstract only).
Becker, T.W. et al., The cab-m7 gene: a light-inducible, mesophyll-specific gene of maize, 20(1) Plant Mol Biol. 49-60 (1992) (Abstract only).

(Continued)

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A miniature rose plant named 'MEIBENBINO' is disclosed. Embodiments include seeds of 'MEIBENBINO', plants of 'MEIBENBINO', plant parts of 'MEIBENBINO', methods for producing a rose plant by crossing 'MEIBENBINO' with itself or with another rose plant variety, and methods for producing other rose plant lines or plant parts derived from 'MEIBENBINO', and the rose plants, varieties, and their parts derived from the use of those methods. Also disclosed are methods for producing a rose plant containing the genetic material of one or more genes or transgenes and transgenic rose plants and plant parts produced by those methods. In addition, rose varieties, breeding varieties, plant parts, and cells derived from rose plant 'MEIBENBINO' are disclosed.

5 Claims, 1 Drawing Sheet
(1 of 1 Drawing Sheet(s) Filed in Color)

(56) References Cited

OTHER PUBLICATIONS

Burton, R. et al., Virus-Induced Silencing of a Plant Cellulose Synthase Gene, 12 The Plant Cell 691-705 (2000).
Charest, P.J. et al., In vitro study of transgenic tobacco expressing Arabidopsis wild type and mutant acetohydroxyacid synthase genes, 8(11) Plant Cell Rep. 643-646 (1990) (Abstract only).
Creissen, G. et al., Molecular characterization of glutathione reductase cDNAS from pea (*Pisum sativum* L.), 2(1) The Plant Journal 129-131 (1991).
Daboussi. F. et al., Engineering Meganuclease for Precise Plant Genome Modification, Advances in New Technology for Targeted Modification of Plant Genomes 21-38 {2015}{Abstract only).
De Block, M. et al., Expression of foreign genes in regenerated plants and in their progeny, 3(8) The EMBO Journal 1681-1689 (1984).
Dhir, S.K. et al., Regeneration of fertile plants from protoplasts of soybean (*Glycine max* L. Merr.): genotypic differences in culture response, 11(506) Plant Cell Rep. 285-289 (1992) (Abstract only).
Eichholtz, D.A. et al., Expression of mouse dihydrofolate reductase gene confers methotrexate resistance in transgenic petunia plants, 13(1) Somat Cell Mol Genet. 67-76 (1987) (Abstract only).
Ferrie, A. et al., Review of Doubled Haploidy Methodologies in Ornamental Specie, 11(2) Propagation of Ornamental Plants 63-77 (2011) (References).
Flavell, R.B., Inactivation of gene expression in plants as a consequence of specific sequence duplicaiton, 91 Proc. Natl. Acad. Sci. USA 3490-3496 (1994).
Fletcher, R. et al., QTL analysis of root morphology, flowering time, and yield reveals trade-0ffs in response to drought n *Brassica napus*, 66(1) Journal of Experimental Botany 245-256 (2014).
Frontes, E. et al., Characterization of an Immunoglobulin Binding Protein Homolog in the Maize floury-2 Endosperm Mutant, 3 The Plant Cell 483-496 (1991).
Gibson, S.A. et al., Ribozymes. Their functions and strategies for their use, 7(2) Mol. Biotech 125-137 (1997) (Abstract only).
Gould, S. et al., A Conserved Tripeplide Sorts Proteins to Peroxisomes, 108 The Journal of Cell Biology 1657-1664 (1989).
Haseloff, J. et al., Simple RNA enzymes with new and highly specific endoribonuclease activities, 334(6183) Nature 585-591 (1988) (Abstract only).
Ishino, Y. et al., Nucleotide Sequence of the iap Gene, Responsible for Alkaline Phosphatase Isozyme Conversion in *Escherichia coli*, and Identification of the Gene Product, 169(12) Journal of Bacteriology 5429-5433 (1987).
Jorgensen, R. Altered gene expression in plants due to trans interactions between homologous genes, 8(12) Trends Biotechnol 340-344 (1990) (Abstract only).
Kalderon, D. et al., A short amino acid sequence able to specify nuclear location, 39(3) Cell Press 499-509 (1984) (Abstract only).
Knox, C.A. et al., Structure and organization of two divergent a-amylase genes from barley, 9(1) Plant Mol Biol. 3-17 (1987) (Abstract only).
Komatsuda, T. et al., Genotype X surcose interactions for somatic embryogenesis in soybean, 31(2) Crop Science 333-337 (1991) (Abstract only).
Komatsuda, T. et al., Maturation and germination of somatic embryos as affected by sucrose and plant growth regulators in soybeans *Glycine gracilis* Skvortz and *Glycine max* (L.) Merr., 28(1) Plant Cell Tiss Organ Cult 103-113 (1992) (Abstract only).
Koncz, C. et al., Expression and assembly of functional bacterial luciferase in plants, 84 Proc. Natl. Acad. Sci. USA 131-135 (1987).
Lemer, D. et al., Cloning and Characterization of Root-Specific Barley Lectin, 91 Plant Physiol. 124-129 (1989).

Martinelli, F. et al., Proposal of a Genome Editing System for Genetic Resistance to Tomato Spotted Wilt Virus, 11(11) American Journal of Applied Sciences 1904-1913 (2014).
Matsuoka, K. et al., Propeplide of a precursor to a plant vacuolar protein required for vacuolar targeting, 88 Proc. Natl. Acad. Sci. USA 834-838 (1991).
Montgomery, M. et al., RNA as a target of double-stranded RNA-mediated genetic interference in Caenorhabditis elegans, 95 Proc. Natl. Acad. Sci. USA 15502-15507 (1998).
Napoli, C. et al., Introduction of a Chimeric Chalcone Synthase Gene into Petunia Results in Reversible Co-Suppression of Homologous Genes in trans, 2 The Plant Cell 279-289 (1990).
Neuhuber, F. et al., Susceptibility of transgene loci to homology-dependent gene silencing, 244(3) Mol Gen Genet. 230-241 (1994) (Abstract only).
Noman, A. et al., CRISPR-Cas9: Tool for Qualitative and Quantitative Plant Genome Editing, 7 (1740) Frontiers in Plant Science 1-17 (2016).
Perriman, R. et al., A ribozyme that enhances gene suppression in tobacco protoplasts., 3(3) Antisense Res Dev. 253-263 (1993) (Abstract only).
Petolino, J., Genome editing in plants via designed zinc finger nucleases, 51 In Vitro Cell Dev Biol. 1-8 (2015).
Rego, L. et al., Tissue culture in ornamental plant breeding: A review, 1(3) Crop Breeding and Applied Biotechnology 283-300 (2001).
Sander, J. et al., CRISPR-Cas systems for editing, regulating and targeting genomes, 32(4) Nature Biotechnology 347-355 (2014).
Shah, D. et al., Engineering Herbicide Tolerance in Transgenic Plants, 233(4762) Science 478-481 (1986).
Sharp, P., RNAi and double-strand RNA, 13 Genes Dev. 139-141 (1999).
Sheehy, R. et al., Reduction of polygalacturonase activity in tomato fruit by antisense RNA, 85 Proc. Natl. Acad. Sci. USA 8805-8809 (1988).
Shetty, K. et al., Stimulation of in vitro shoot organogenesis in *Glycine max* (Merrill.) by allantion and amides, 81(2) Plant Science 245-251 (1992) (Abstract only).
Sikora, P. et al., Mutagenesis as a Tool in Plant Genetics, Functional Genomics, and Breeding, 2011 International Journal of Plant Genomics 1-12 (2011).
Smith, N.A. et al., Total silencing by intron-spliced hairpin RNAs, 407 Nature 319-320 (2000).
Sorek, R. et al., CRISPR-Medialed Adaptive Immune Systems in Bacteria and Archaea, 82 Annual Review of Biochemistry 237-266 (2013).
Steifel, V. et al., Expression of a Maize Cell Wall Hydroxyproline-Rich Glycoprotein Gene in Early Leaf and Root Vascular Differentiation, 2 The Plant Cell 785-793 (1990).
Steinecke, P. et al., Expression of a chimeric ribozyme gene results in endonucleolytic cleavage of target mRNA and a concomitant reduction of gene expression in vivo, 11(4) The EMBO Journal 1525-1530 (1992).
Stephens, P.A. et al., Agronomic evaluation of tissue-culture-derived soybean plants, 82(5) Theoretical and Applied Genetics 633-635 (1991) (Abstract only).
Vainslein, A. Ed. Breeding for Ornamentals: Classical and Molecular Approaches, Springer Science+Business Media, B.V. 1-7 (2002) (Table of Contents and Preface Only).
Wang, S. et al., Efficient targeted mutagenesis in potato by the CRISPR/Cas9 system, 34 Plant Cell Rep. 1473-1476 (2015).
Zamore, P. et al., RNAi: Double-Stranded RNA Directs the ATP-Dependent Cleavage of mRNA at 21 to 23 Nucleotide Intervals, 101 Cell 25-33 (2000).
Zhang, B. et al., Exploiting the CRISPR/Cas9 System for Targeted Genome Mutagenesis in Petunia, 6 (20315) Scientific Reports 1-8 (2016).

* cited by examiner

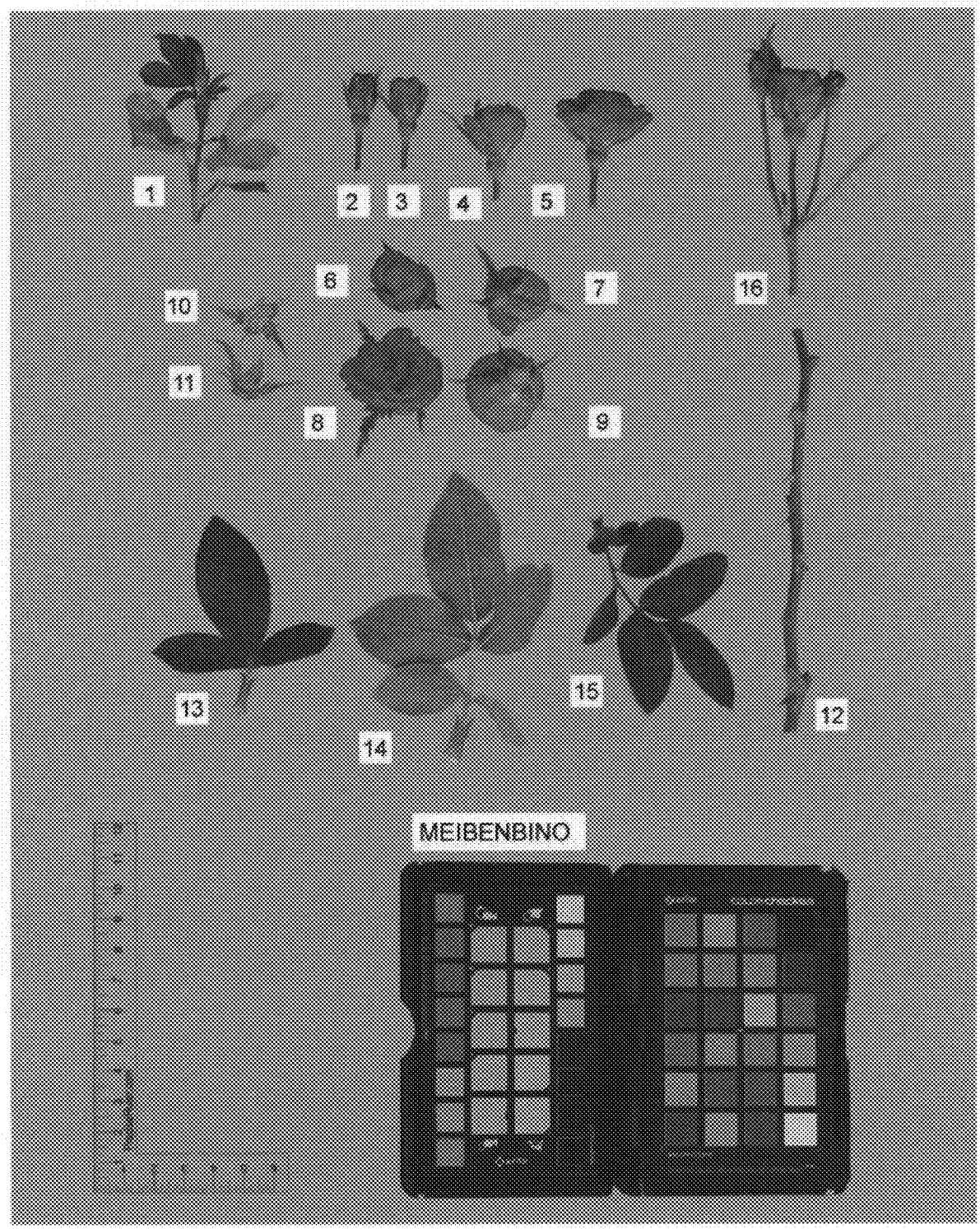

MINIATURE ROSE PLANT NAMED 'MEIBENBINO'

CROSS-REFERENCE TO RELATED APPLICATIONS

This application is a continuation-in-part application of U.S. patent application Ser. No. 16/544,290, filed on Aug. 19, 2019, now U.S. Pat. No. 11,252,928, which is a continuation-in-part application of U.S. Plant patent application Ser. No. 15/932,925, filed on May 23, 2018, now U.S. Plant patent Ser. No. PP30,811, which are incorporated herein by reference in its entirety for all purposes and claims priority under 35 U.S.C. § 119(f) to Community Plant Variety Rights application number 2017/2341 filed on Sep. 21, 2017.

BACKGROUND

The citation of any publication is for its disclosure prior to the filing date and should not be construed as an admission that the present invention is not entitled to antedate such publication by virtue of prior invention. The foregoing examples of the related art and limitations related therewith are intended to be illustrative and not exclusive.

*Rosa hybrida* (rose plant) is a species of flowering plants in the family Rosaceae.

Rose plants can be propagated from many means including seed, cuttings, and tissue culture. Seed, cuttings, and tissue culture germination protocols for Rose plants are well-known in the art.

Rose plants are an important and valuable ornamental plant. Thus, a continuing goal of ornamental plant breeders is to develop plants with novel characteristics, such as color, growth habit, disease tolerance, and hardiness. To accomplish this goal, the breeder must select and develop plants that have traits that result in superior rose varieties.

BRIEF DESCRIPTION OF THE PHOTOGRAPH

The patent or application file contains at least one drawing executed in color. Copies of this patent or patent application publication with color drawing(s) will be provided by the Office upon request and payment of the necessary fee.

The accompanying photographs of FIG. 1 show as nearly true as it is reasonably possible to make the same, in a color illustration of this character, typical specimens of the plant parts of the 'MEIBENBINO' variety. The rose plants of 'MEIBENBINO' were approximately one year of age and were observed during July while budded on their own roots and growing outdoors at Le Cannet des Maures, Var, France. Standard color information and dimensions in centimeters are included at the bottom of FIG. 1.

Element 1—illustrates a specimen of a young shoot.
Element 2—illustrates a specimen of a floral bud before the opening of the sepals.
Element 3—illustrates a specimen of a floral bud at the opening of the sepals.
Element 4—illustrates a specimen of a floral bud at the opening of the petals.
Element 5—illustrates a specimen of a flower in the course of opening.
Element 6—illustrates a specimen of a flower in the course of opening—plan view—obverse.
Element 7—illustrates a specimen of a flower in the course of opening—plan view—reverse.
Element 8—illustrates a specimen of a fully open flower—plan view—obverse.
Element 9—illustrates a specimen of a fully open flower—plan view—reverse.
Element 10—illustrates a specimen of a floral receptacle showing arrangement of the stamens and pistils.
Element 11—illustrates a specimen of a floral receptacle showing arrangement of the pistils (stamens removed).
Element 12—illustrates a specimen of a flowering stem.
Element 13—illustrates a specimen of a leaf with 3 leaflets—plan view—upper surface.
Element 14—illustrates a specimen of a leaf with 5 leaflets—plan view—under surface.
Element 15—illustrates a specimen of a leaf with 7 leaflets—plan view—upper surface.
Element 16—illustrates a specimen of buds in cluster.

SUMMARY

It is to be understood that this invention is not limited to particular embodiments described, as such may, of course, vary. The following embodiments and aspects thereof are described in conjunction with systems, tools, and methods which are meant to be exemplary, not limiting in scope.

According to one embodiment, there is provided a new and distinct variety of miniature rose plant, named 'MEIBENBINO', characterized by the following combination of characteristics: (a) very abundantly and nearly continuously forms attractive, cup-shaped, red colored blossoms, (b) forms attractive, very dense, glossy foliage, (c) exhibits very good tolerance to diseases, particularly against Black Spot, and (d) is well suited for providing attractive ornamentation; substantially as shown and described herein.

According to one embodiment, there is provided a rose plant 'MEIBENBINO' which is valued as breeding line enabling the development of superior ornamental rose plants.

Another embodiment discloses a rose plant 'MEIBENBINO', wherein a sample of representative sample of plant tissue of said rose plant is to be deposited.

Another embodiment discloses a rose plant having all of the physiological and morphological characteristics of a rose plant of variety 'MEIBENBINO'.

Another embodiment relates to a method of producing a rose plant, said method comprising cultivating a plant part comprising at least one cell of the rose plant variety 'MEIBENBINO'.

Another embodiment relates to tissue or cell culture of regenerable cells produced from a rose plant of variety 'MEIBENBINO'. A further embodiment relates to a rose plant regenerated from the tissue or cell culture of 'MEIBENBINO'.

Another embodiment relates to tissue or cell culture produced from tissues, protoplasts, or cells from the rose plants disclosed in the subject application. In further embodiments, said tissues, cells, or protoplasts are produced from a plant part selected from the group consisting of pollen, embryos, protoplasts, meristematic cells, callus, pollen, leaves, ovules, anthers, cotyledons, hypocotyl, pistils, roots, root tips, flowers, seeds, petiole, and stems.

Another embodiment relates to a method of vegetatively propagating the plant of variety 'MEIBENBINO', comprising the steps of: collecting tissue or cells capable of being propagated from a plant of 'MEIBENBINO'; cultivating said tissue or cells to obtain proliferated shoots; and rooting said proliferated shoots to obtain rooted plantlets; or cultivating said tissue or cells to obtain proliferated shoots, or to obtain plantlets and a plant produced by growing the plantlets or proliferated shoots of said plant.

Another embodiment relates to methods of developing a rose plant variety having the physiological and morphological characteristics of a rose plant of variety 'MEIBENBINO', said method comprising genotyping a rose plant of variety 'MEIBENBINO', wherein said genotyping comprises obtaining a sample of nucleic acids from said plant and detecting in said nucleic acids a plurality of polymorphisms, and using said identified polymorphisms for marker assisted selection in a breeding program.

Another embodiment relates to a method for developing a rose plant variety, comprising identifying and selecting a spontaneous mutation of a rose plant of variety 'MEIBENBINO' or a part thereof, and cultivating said selected spontaneous mutation plant or plant part. A further embodiment relates to a rose plant produced by cultivating said selected spontaneous mutation plant or plant part.

Another embodiment relates to a method for developing a rose plant variety, comprising introducing a mutation into the genome of a plant of variety 'MEIBENBINO' or a part thereof, and cultivating said mutated plant or plant part. A further embodiment relates to a rose plant produced by cultivating said mutated plant or plant part. In a further embodiment, said mutation is introduced using a method such as temperature, long-term seed storage, tissue culture conditions, ionizing radiation, chemical mutagens, targeting induced local lesions in genomes, zinc finger nuclease mediated mutagenesis, CRISPR/Cas-9, meganucleases, or gene editing.

Another embodiment relates to a method for developing a rose plant variety, comprising transforming a rose plant of variety 'MEIBENBINO' with a transgene. In a further embodiment, said transgene confers resistance to an herbicide, insecticide, or disease. A further embodiment relates to an herbicide, insecticide, or disease resistant plant produced by the method for developing a rose plant variety, comprising transforming a rose plant of variety 'MEIBENBINO' with a transgene.

Another embodiment relates to a method of producing an $F_1$ seed or embryo, wherein the method comprises crossing a rose plant of variety 'MEIBENBINO' with a second plant and harvesting the resultant $F_1$ seed or embryo. In a further embodiment, said second plant comprises another plant of variety 'MEIBENBINO'. In a different further embodiment, said second plant is a plant of a different variety than 'MEIBENBINO'. Another further embodiment relates to a rose plant produced by cultivating the harvested $F_1$ seed or embryo produced by a method comprises crossing a rose plant of variety 'MEIBENBINO' with a second plant and harvesting the resultant $F_1$ seed or embryo.

A further embodiment relates to a method for producing an $F_1$ rose seed, wherein the method comprises crossing a 'MEIBENBINO' plant with a different rose plant variety and harvesting the resultant $F_1$ rose seed.

A further embodiment relates to a method for developing a rose plant in a rose plant breeding program, comprising applying plant breeding techniques. In further embodiments plant breeding techniques include recurrent selection, backcrossing, pedigree breeding, marker enhanced selection, or transformation to the rose plant of 'MEIBENBINO', or its parts, wherein application of said techniques results in development of a new rose plant variety.

In addition to the exemplary aspects and embodiments described above, further aspects and embodiments will become apparent by study of the following descriptions.

Definitions

"Allele" is any of one or more alternative forms for a gene.

As used herein, "gene" refers to a segment of nucleic acid.

A "locus" is the position or location of a gene on a chromosome.

By "plant parts" or "rose plant part" or "a part thereof" is meant to refer to any part of the plant and includes but is not limited to, regenerable cells which may include plant calli, plant clumps, plant protoplast, plant cells, embryos, protoplasts, meristematic cells, callus, pollen, leaves, ovules, anthers, cotyledons, hypocotyl, pistils, roots, root tips, fruit, flowers, seeds, shoot, petiole, or stems.

As used herein, "progeny" is the descendants of one or more of the parental lines and includes an $F_1$ rose plant produced from the cross of two rose plants where at least one plant includes a rose plant disclosed herein and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line.

As used herein, "regeneration" refers to the development of a plant from tissue culture or cell culture.

As used herein, "single gene converted plants" or "single gene conversion plants" or "backcross conversion plants" or "backcross converted plants" refers to plants which are developed by a plant breeding technique called backcrossing wherein essentially all of the desired morphological and physiological characteristics of a variety are recovered via the backcrossing technique in addition to the single gene transferred into the variety via the initial cross or via genetic engineering.

As used herein, "desired trait(s)" or "desired characteristic(s)" or "desired attribute(s)" or "desired gene(s)" or "desired phenotype(s)" refers to a phenotypical characteristic or genomic characteristic which is identified in a plant.

As used herein, "sport" or "spontaneous mutation" or "natural mutation" refers to a mutation which has arisen spontaneously and has not been induced. These mutations may be selected from the initial variety and cultivated to produce an essentially derived variety. Sports, spontaneous mutations, and natural mutations may occur in an individual plant or on a plant part of the initial variety plant.

As used herein, "essentially derived variety" refers to the definitions set forth under 7 U.S.C. § 2401 and UPOV Convention.

As used herein, "crossing" may refer to comprising a simple x by y cross or the process of backcrossing depending on the context and may include additional tools or methods, such as genetic markers.

As used herein, the term "about" refers to a number that differs from the given number by less than 10%. In other embodiments, the term "about" indicates that the number differs from the given number by less than 9%, 8%, 7%, 6%, 5%, 4%, 3%, 2%, or 1%.

DETAILED DESCRIPTION

Origin of 'MEIBENBINO'

'MEIBENBINO' was created by artificial pollination wherein two parents were crossed which previously had been studied in the hope that they would contribute the desired characteristics. The female parent (i.e., the seed parent) was the product of a cross of the 'MEIPAONIA' variety (non-patented in the United States) and an 'UNNAMED SEEDLING' variety. The male parent (i.e., the pollen parent) was the 'RADTKO' variety (U.S. Plant Patent Ser. No. 16,202).

The parentage of the new variety can be summarized as follows:

('MEIPAONIA' x 'UNNAMED SEEDLING') x 'RADTKO'

The seeds resulting from the above pollination were sown and small plants were obtained which were physically and biologically different from each other. Selective study resulted in the identification of a single plant of the new variety.

This new variety has been named 'MEIBENBINO'.

It was found that the 'MEIBENBINO' variety of the present invention possesses the following combination of characteristics:

(a) very abundantly and nearly continuously forms attractive, cup-shaped, red colored blossoms, (b) forms attractive, very dense, glossy foliage, (c) exhibits very good tolerance to diseases, particularly against Black Spot, and (d) is well suited for providing attractive ornamentation.

The 'MEIBENBINO' variety well meets the needs of the horticultural industry. It can be grown to advantage as ornamentation in parks, gardens, public areas, and in residential settings. Accordingly, the 'MEIBENBINO' plant is particularly well suited for growing in the landscape.

The 'MEIBENBINO' variety of the present invention can readily be distinguished from its ancestors. More specifically, the 'RADTKO' variety (i.e., the pollen parent) is a shrub rose plant/bedding rose plant, whereas the 'MEIBENBINO' variety is a miniature rose plant. The ('MEIPAONIA' x 'UNNAMED SEEDLING') variety (i.e., the seed parent) exhibits bigger flowers with more petals compared to the 'MEIBENBINO' variety and provides ocher colored blossoms, whereas the 'MEIBENBINO' variety exhibits red colored blossoms. The 'MEIPAONIA' variety (i.e., a parent of the seed parent) exhibits ocher colored blossoms, whereas the 'MEIBENBINO' variety exhibits red colored blossoms.

The 'MEIBENBINO' variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

DETAILED BOTANICAL DESCRIPTION OF 'MEIBENBINO'

The chart used in the identification of the colors is that of The Royal Horticultural Society (The R.H.S. Color Chart), London, England. The terminology which precedes reference to the chart has been added to indicate the corresponding color in more common terms. The description is based on the observation of one-year-old specimens of the new variety during July while budded on their own roots and growing outdoors at Le Cannet des Maures, Var, France.

Botanical/Commercial Classification
   Latin name—*Rosa hybrida*
   Common name—Miniature Rose Plant
   Varietal Denomination—'MEIBENBINO'
Class
   Miniature Rose Plant
Plant
   habit—semi-erect.
   height—commonly near 35 cm on average.
   diameter—commonly near 35 cm on average.
Branches
   stem size—length is commonly between 20 to 35 cm on average; diameter is commonly between 0.3 to 0.7 cm on average.
   color—young stems: commonly near Yellow-Green Group 147C.
      adult wood: commonly near Yellow-Green Group 146C.
   thorns—configuration on adult stems: rather upright on the upper surface and slightly concave on the under surface.
      long prickles (>0.6 cm)—quantity: commonly approximately 5 thorns per 10 cm long young stem and approximately 6 thorns per 10 cm long adult stem.
      long prickles (0.6 cm)—base shape: oval.
      long prickles (0.6 cm)—size: commonly near 0.6 cm in length on average on young stems and commonly near 0.7 cm in length on average on adult stems.
      long prickles (0.6 cm)—color commonly near Yellow-Green Group 147D on young stems and commonly near Greyed-Orange Group 164A on adult stems.
      small prickles (<0.6 cm)—none observed.
Foliage
   general appearance—very dense with a glossy aspect.
   number of leaflets—3, 5, and 7; most often 5 or 7.
   terminal leaflet—length: approximately 3.7 cm on average.
      width: approximately 2.3 cm on average.
   typical leaf—length: typically between 8.5 to 12 cm on average.
      width: typically between 6.0 to 8.0 cm on average.
   new foliage—upper surface color commonly near Yellow-Green Group 147B.
      under surface color commonly near Yellow-Green Group 146C.
   adult foliage—upper surface color commonly near Green Group 137A.
      under surface color commonly near Yellow-Green Group 146B.
Leaflets
   shape—tip: acuminate.
      base: cuneiform.
   texture—leathery.
   general appearance—elliptical.
   edge—slightly denticulate.
   serration—small and single.
   petiole rachis—color of upper surface: commonly near Greyed-Orange Group 164A.
      color of under surface: commonly near Yellow-Green Group 146B.
      length: typically between 3.0 to 5.0 cm on average.
      diameter approximately 0.1 cm on average.
   petioles—upper surface: no glandular.
      under surface: few prickles.
      color of upper surface: commonly near Yellow-Green Group 146B.

color of under surface: commonly near Yellow-Green Group 146B.
diameter typically between 0.1 to 0.2 cm on average.
petiole length of terminal leaflet: commonly near 1.9 cm on average.
stipules—general appearance: adnate, pectinate and narrow; represents half of the petiole.
apex: long; length is near 0.5 cm and width is typically between 0.1 to 0.2 cm on average.
base: not observed.
length: approximately 0.7 cm on average.
width: approximately 0.3 cm on average.
color of upper surface: commonly near Yellow-Green Group 146B.
color of under surface: commonly near Yellow-Green Group 146B.

Inflorescence
number of flowers per stem—generally between 1 and 6 flowers per stem; typically between 1 and 6 flowers per cluster.
bud—shape: conical.
size: small.
length: approximately 1.0 cm on average.
width: approximately 0.9 cm on average.
color as calyx breaks:
upper surface: commonly near Red Group 46B to Red Group 46A.
under surface: commonly near Red Group 46B to Red Group 46A.
sepals—number commonly 5.
length: approximately between 1.3 cm on average.
width: approximately near 0.4 cm on average.
shape: some longish and narrow denticulate extensions; extensions are typically between 0.2 to 1.0 cm of length,
at the top: longish and narrow,
at the base: upright.
upper surface:
texture: tomentous.
color commonly near Yellow-Green Group 148C.
under surface:
texture: smooth.
color commonly near Yellow-Green Group 146A.
receptacle—color commonly near Yellow-Green Group 146A.
length: approximately 0.6 cm on average.
width: approximately 0.7 cm on average.
surface: smooth.
shape: funnel shaped.
peduncle—length: approximately 2.7 to 3.3 cm on average.
width: approximately 0.3 cm on average.
surface: smooth.
color commonly near Yellow-Green Group 146A.
flower—average diameter when fully open: approximately 3.0 to 3.5 cm on average.
depth: commonly near 2.0 cm on average.
borne: commonly between 1 to 5 flowers per stem.
shape: cup shaped.
number of petals under normal conditions: approximately 9 to 12 petals on average.
shape of the petal: cordiform.
base: obtuse.
top: rounded.
texture of the petal: leathery.
petallength: approximately 2.4 cm on average.
petal width: approximately 2.2 cm on average.
petal arrangement: imbricated with some petaloids.
petal drop: petals drop off cleanly before drying.
petal margin: slightly undulated.
fragrance: none.
color when opening:
upper surface: commonly near Red Group 46B to Red Group 46A, very little spot at the base commonly near Yellow Group 13D.
under surface: commonly near Red Group 46B to Red Group 46A, very little spot at the base commonly near Yellow Group 13D.
color of the open flower:
upper surface: commonly near Red Group 46B to Red Group 46A, very little spot at the base commonly near Yellow Group 13D.
under surface: commonly near Red Group 46B to Red Group 46A, very little spot at the base commonly near Yellow Group 13D.
petaloids: number is commonly 3 to 5; length is commonly between 1.0 to 2.0 cm on average; width is commonly between 0.5 to 1.5 cm on average; shape is cordiform or half cordiform; commonly very undulated; have filament at the base; and color is commonly between Red Group 46A and Red Group 46B.
anthers: number is approximately 52 on average, length is approximately 0.1 cm on average, coloration is commonly near Greyed-Orange Group 173B, and arrangement is regular around styles.
filaments: length is approximately near 0.3 cm on average and coloration is commonly near Red Group 42D.
styles: length is approximately 0.4 cm on average, the coloration is commonly near Red Group 44C, and the number is approximately 32 on average.
stigmas: size is approximately 0.1 cm on average and the coloration is commonly near Yellow Group 12D.
pollen: not available at this stage.
hips: not available at this stage.

Development
vegetation—strong.
winter hardiness—Zone 5.
blooming—early in the season, very abundant and nearly continuous.
tolerance to disease—very good, and particularly against Black Spot.

The new 'MEIBENBINO' variety has not been observed under all possible environmental conditions to date. Accordingly, it is possible that the phenotypic expression may vary somewhat with changes in light intensity and duration, cultural practices, and other environmental conditions.

Breeding with Rose 'MEIBENBINO' Variety

The goal of ornamental plant breeding is to develop new, unique, and superior ornamental plants. The breeder typically selects and crosses two or more parental lines, followed by selection, producing many new genetic combinations. The breeder can theoretically generate billions of different genetic combinations via crossing, selection, selfing, and/or mutagenesis.

Due to the large number of possible genetic combinations that result from such a cross, it is often difficult to reproduce a variety with a particular desired trait by simply crossing the same original parents and utilizing the same selection techniques. This unpredictability results in the expenditure of large amounts of research funds to develop superior rose varieties. To advance breeding programs more quickly, breeders often use a variety that contains the desired trait as a parental line as a starting point rather than trying to recreate the variety possessing that desired trait.

Breeding programs combine desirable traits from two or more varieties or various broad-based sources into breeding pools from which varieties are developed and selected for desired phenotypes. Breeding programs may include artificial pollination wherein two parents are crossed which previously had been studied in the hope that the parents would contribute the desired characteristics. Seeds resulting from such an artificial pollination can be sown to obtain small plants, and then selective study can be used to identify a new plant variety which includes the desired phenotype.

Pedigree breeding is commonly used for the improvement of self-pollinating plants. An example of pedigree breeding is when two parents that possess favorable traits are crossed to produce an $F_1$. Then an $F_2$ population is produced by selfing one or several $F_1$s. This is followed by selection of the best individuals which may begin in the $F_2$ population; then, often beginning in the $F_3$, the best individuals in the best families are selected. Replicated testing of families may often begin in the $F_4$ generation to improve the effectiveness of selection for traits with low heritability. At an advanced stage of inbreeding, the best lines or mixtures of phenotypically similar lines may be further tested for selection of new varieties.

Using Rose Plant 'MEIBENBINO' to Develop Other Plants

'MEIBENBINO' plants can also provide a source of breeding material that may be used to develop new rose plants and varieties. Plant breeding techniques known in the art and used in a rose plant breeding program include, but are not limited to, recurrent selection, mass selection, bulk selection, hybridization, mass selection, backcrossing, pedigree breeding, open-pollination breeding, restriction fragment length polymorphism enhanced selection, genetic marker enhanced selection, mutagenesis, and transformation. Combinations of these techniques may be used. There are many analytical methods available to evaluate a new variety. The traditional method of analysis is the observation of phenotypic traits, but genotypic analysis may also be used.

Additional Breeding Methods

Any plants produced using 'MEIBENBINO' disclosed in the present application as at least one parent are further embodiments of the present invention. Thus, plants which contain about 50% of the genetic composition of 'MEIBENBINO' are another embodiment of the present invention. Methods for producing progeny using 'MEIBENBINO' as at least one of the parents are well-known in the art and some of the more commonly used breeding methods are described herein. Descriptions of breeding methods are well-known in the art and may be found in several reference books, e.g., Vainstein, "Breeding for Ornamentals: Classical and Molecular Approaches," Kluwer Academic Publishers (2002).

Breeding steps that may be used in the rose 'MEIBENBINO' plant breeding program can include, for example, artificial pollination using 'MEIBENBINO' as at least one of the parents, pedigree breeding, backcrossing, and recurrent selection. In conjunction with these steps, techniques such as mutagenesis, RFLP-enhanced selection, genetic marker enhanced selection (for example, SSR markers), and gene editing may be utilized.

Pedigree Breeding

Pedigree breeding starts with the crossing of two genotypes, such as 'MEIBENBINO' and another different rose variety having one or more desirable characteristics that is lacking or which complements the 'MEIBENBINO' phenotype. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

Backcross Breeding

Backcross breeding has been used to transfer genes for a simply inherited, highly heritable trait into a desirable homozygous variety or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent and the desirable trait transferred from the donor parent. This is also known as single gene conversion and/or backcross conversion.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good commercial characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, a rose plant, such as 'MEIBENBINO' may be crossed with another variety to produce a first generation progeny plant. The first generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new rose varieties.

Therefore, another embodiment is a method of making a backcross conversion of 'MEIBENBINO', comprising the steps of crossing 'MEIBENBINO' with a donor plant comprising a desired trait, selecting an $F_1$ progeny plant comprising the desired trait, and backcrossing the selected $F_1$ progeny plant to 'MEIBENBINO'. This method may further comprise the step of obtaining a molecular marker profile of 'MEIBENBINO' and using the molecular marker profile to select for a progeny plant with the desired trait and the molecular marker profile of 'MEIBENBINO'.

Recurrent Selection and Mass Selection

Recurrent selection is a method used in a plant breeding program to improve a population of plants. 'MEIBENBINO' is suitable for use in a recurrent selection program. The method entails individual plants cross-pollinating with each other to form progeny. The progeny are grown and the superior progeny, which include individual plant, half-sib progeny, full-sib progeny, and selfed progeny, are selected by any number of selection methods. The selected progeny are cross-pollinated with each other to form progeny for another population. This population is planted and again superior plants are selected to cross-pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties.

Mass selection is a useful technique especially when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating plants. A genetically variable population of heterozygous individuals is either identified, or created, by intercrossing several different parents. The best plants are selected based on individual superiority, outstanding progeny, or excellent combining ability. The selected plants may then be intercrossed to produce a new population in which further cycles of selection are continued.

Essentially Derived Varieties

Mutations that occur spontaneously or are artificially induced can be useful sources of variability for a plant breeder. An essentially derived variety is predominantly derived from the initial variety, or from a variety that is itself predominantly derived from the initial variety, while retaining the expression of the essential characteristics that result from the genotype or combination of genotypes of the initial variety; is clearly distinguishable from the initial variety; and except for the differences which result from the act of derivation, it conforms essentially to the initial variety in the expression of the essential characteristics that result from the genotype or combination of genotypes of the initial variety. An essentially derived variety may be obtained by the selection of a natural mutant (e.g., spontaneous mutant, also referred to as a sport) or induced mutant or of a somaclonal variant, the selection of a variant individual from plants of the initial variety, backcrossing, transformation by genetic engineering, or other methods.

Therefore, another embodiment is to an essentially derived variety of 'MEIBENBINO'. A further embodiment is to methods of artificially inducing an essentially derived variety from 'MEIBENBINO'.

Mutagenesis

The goal of artificial mutagenesis is to increase the rate of mutation for a desired characteristic. Mutation rates can be increased by many different means including, but not limited to temperature, long-term seed storage, tissue culture conditions, ionizing radiation, such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm); chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates such as ethyl methanesulfonate, sulfones, lactones), sodium azide, hydroxylamine, nitrous acid, methyl-nitrilsourea, or acridines; and/or TILLING (targeting induced local lesions in genomes), wherein mutation is induced typically by chemical mutagens and the mutagenesis is accompanied by the isolation of chromosomal DNA from the mutated plant lines or seeds and then screening of the population of the seeds or plants is performed at the DNA level using molecular techniques. Once a desired trait is observed through mutagenesis the trait may then further be incorporated into existing germplasm by traditional breeding techniques.

Details of breeding with mutagenesis or a mutant variety can be found, for example, in the following: Vainstein, *Breeding for Ornamentals: Classical and Molecular Approaches*, (2002) KLUWER ACADEMIC PUBLISHERS; Sikora, et al., *Mutagenesis as a Tool in Plant Genetics, Functional Genomics, and Breeding*, 2011 INTERNATIONAL JOURNAL OF PLANT GENOMICS, 13 pages; Petilino, Genome editing in plants via designed zinc finger nucleases (2015) IN VITRO CELL DEV BIOL PLANT. 51(1): 1-8; and Daboussi, et al., *Engineering Meganuclease for Precise Plant Genome Modification*, "Advances in New Technology for Targeted Modification of Plant Genomes" (2015). SPRINGER SCIENCE+BUSINESS. 21-38. In addition, mutations created in other rose plants may be used to produce a backcross conversion using 'MEIBENBINO'.

Gene Editing

Gene editing can be done through a variety of techniques including zinc finger nucleases and CRISPR/Cas9 technology. See e.g., Saunders & Joung, NATURE BIOTECHNOLOGY, 32, 347-355, 2014. CRISPR is a type of targeted genome editing system that stands for Clustered Regularly Interspaced Short Palindromic Repeats. This system and CRISPR-associated (Cas) genes naturally enable organisms, such as select bacteria and archaea, to respond to and eliminate invading genetic material. See e.g., Ishino, et al., J. BACTERIOL. 169, 5429-5433 (1987). CRISPR/Cas9 technology is used for direct gene editing, in vivo and in vitro. Many plants have already been modified using the CRISPR system. See e.g., International Publication No. WO2014/068346; Martinelli, et al., *Proposal of a Genome Editing System for Genetic Resistance to Tomato Spotted Wilt Virus* 2014 AMERICAN JOURNAL OF APPLIED SCIENCES; Noman, et al., *CRISPR-Cas9: Tool for Qualitative and Quantitative Plant Genome Editing*, November 2016 FRONTIERS IN PLANT SCIENCE Vol. 7; and Zhang et al., *Exploiting the CRISPR/Cas9 System for Targeted Genome Mutagenesis in Petunia* February 2016 SCIENCE REPORTS Volume 6.

Additional information about CRISPR/Cas9 system technology including crRNA-guided surveillance complex systems for gene editing may be found in the following documents: U.S. Application Publication No. 2010/0076057; U.S. Application Publication No. 2014/0179006; U.S. Pat. No. 10,000,772; U.S. Application Publication No. 2014/0294773; Sorek et al., ANNU. REV. BIOCHEM. 82:273-266, 2013; and Wang, S. et al., PLANT CELL REP (2015) 34: 1473-1476. Therefore, it is another embodiment to use gene editing, including the CRISPR/Cas9 system, on 'MEIBENBINO' to modify traits, such as hardiness and resistances or tolerances to pests, herbicides, diseases, and viruses.

Introduction of a New Trait or Locus into 'MEIBENBINO'

'MEIBENBINO' represents a new base of genetics into which a new locus or trait may be introgressed or introduced. Direct transformation and backcrossing represent two important methods that can be used to accomplish such an introgression. The term backcross conversion and single locus conversion are used interchangeably to designate the product of a backcrossing program.

Transformation

Transformation methods include, but are not limited to, expression vectors introduced into plant tissues using a gene transfer method, such as microprojectile-mediated delivery, DNA injection, electroporation, and the like. In some embodiments, expression vectors are introduced into plant tissues of 'MEIBENBINO' by using either microprojectile-mediated delivery with a biolistic device or by using Agrobacterium-mediated transformation. Accordingly further embodiments are methods of transformation using 'MEIBENBINO' and the transformant plants obtained with the protoplasm of the subject 'MEIBENBINO' plants.

Expression Vectors for 'MEIBENBINO' Transformation: Marker Genes

Plant transformation typically involves the construction of an expression vector which will function in plant cells. Such expression vectors comprise DNA comprising a gene under control of, or operatively linked to, a regulatory element (e.g., a promoter). Expression vectors typically include at least one genetic marker operably linked to a regulatory element that allows transformed cells containing the marker to be either recovered by negative selection (e.g., inhibiting growth of cells that do not contain the selectable marker gene) or by positive selection (e.g., screening for the product encoded by the genetic marker). Commonly used selectable marker genes for plant transformation are well-known in the art, and include, for example, genes that code for enzymes that metabolically detoxify a selective chemical agent which may be an antibiotic or an herbicide, or genes that encode an altered target which is insensitive to the inhibitor. Positive selection methods are also known in the art.

One commonly used selectable marker gene for plant transformation is the neomycin phosphotransferase II (nptII) gene which, when under the control of plant regulatory signals, confers resistance to kanamycin. Another commonly used selectable marker gene is the hygromycin phosphotransferase gene which confers resistance to the antibiotic hygromycin.

Selectable marker genes for plant transformation not of bacterial origin include, for example, mouse dihydrofolate reductase, plant 5-enolpyruvylshikimate-3-phosphate synthase, and plant acetolactate synthase. See, e.g., Eichholtz, et al., SOMATIC CELL MOL. GENET., 13:67 (1987); Shah, et al., SCIENCE, 233:478 (1986); and Charest, et al., PLANT CELL REP., 8:643 (1990).

Another class of marker genes for plant transformation requires screening of presumptively transformed plant cells. Reporter genes are an example of this type of marker genes and can be used to quantify or visualize the spatial pattern of expression of a gene in specific tissues. Moreover, reporter genes can be fused to a gene or gene regulatory sequence for the investigation of gene expression. Commonly used marker genes for screening presumptively transformed cells include β-glucuronidase (GUS), β-galactosidase, luciferase, and chloramphenicol acetyltransferase. See, e.g., Teeri, et al., EMBO J., 8:343 (1989); Koncz, et al., PROC. NATL. ACAD. SCI. USA, 84:131 (1987); and DeBlock, et al., EMBO J., 3:1681 (1984).

Expression Vectors for 'MEIBENBINO' Transformation: Promoters

Genes included in expression vectors must be driven by a nucleotide sequence comprising a regulatory element (e.g., a promoter). Many types of promoters are well known in the art, as are other regulatory elements that can be used alone or in combination with promoters.

Some promoters are under developmental control and include promoters that preferentially initiate transcription in certain tissues, such as leaves, roots, seeds, fibers, xylem vessels, tracheids, or sclerenchyma. Such promoters are typically referred to as "tissue-preferred." Whereas promoters that initiate transcription only in a certain tissue are typically referred to as "tissue-specific." A "cell-type" specific promoter primarily drives expression in certain cell types in one or more organs, for example, vascular cells in roots or leaves. Whereas an "inducible" promoter typically refers to a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter refers to a promoter that is active under most environmental conditions. Many types of promoters are well known in the art.

Additional Transformation Embodiments

The foregoing methods for transformation may be used for producing a transgenic variety. The transgenic variety could then be crossed with another (non-transformed or transformed) variety in order to produce a new transgenic variety. Alternatively, a genetic trait that has been engineered into a particular rose line using the foregoing transformation techniques could be moved into another line using traditional breeding techniques that are well known in the art. For example, a backcrossing approach could be used to move an engineered trait from a publically available variety into an elite variety, such as 'MEIBENBINO', or a backcrossing approach can be used to move a foreign gene from a variety containing the foreign gene in its genome into a variety that does not contain that gene.

Likewise, by means of such embodiments, commercially important genes can be expressed in transformed plants. More particularly, plants can be genetically engineered to express various phenotypes of commercial interest, including, but not limited to, genes that confer resistance to pests or disease, genes that confer resistance to an herbicide, genes that confer or contribute to a value-added or desired trait, genes that control male sterility, genes that create a site for site specific DNA integration, and genes that affect abiotic stress resistance. Many different genes are known and could potentially be introduced into a rose plant according to the invention. Non-limiting examples of particular genes and corresponding phenotypes one may choose to introduce into a rose plant include one or more genes for insect tolerance, such as a Bacillus thuringiensis (Bt.) gene, pest tolerance such as genes for fungal disease control, herbicide tolerance such as genes conferring glyphosate tolerance, and genes for quality improvements such as environmental or stress tolerances, or any desirable changes in plant physiology, growth, development, morphology, or plant product(s). For example, structural genes would include any gene that confers insect tolerance including but not limited to a Bacillus insect control protein gene as described in International Publication No. WO 99/31248, U.S. Pat. Nos. 5,689,052, 5,500,365 and 5,880,275. In another embodiment, the structural gene can confer tolerance to the herbicide glyphosate as conferred by genes including, but not limited to Agrobacterium strain CP4 glyphosate resistant EPSPS gene (aroA:CP4) as described in U.S. Pat. No. 5,633,435, or glyphosate oxidoreductase gene (GOX) as described in U.S. Pat. No. 5,463,175. Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (e.g., a ribozyme) engineered to cleave a desired endogenous mRNA product. See, e.g., Gibson and Shillito, MOL. BIOTECH., 7:125, 1997. Thus, any gene which produces a protein or mRNA which is necessary for a phenotype or morphology change of interest is useful for the practice of one or more embodiments.

Single-Gene Conversions

Single gene conversions of 'MEIBENBINO' are included as embodiments of the present invention. The term single gene converted plant as used herein refers to those rose plants which are developed by backcrossing, wherein in backcrossing essentially all of the desired morphological and physiological characteristics of a variety are recovered in addition to the single gene transferred into the variety via the backcrossing technique. Backcrossing methods can be used with one embodiment of the present application to improve or introduce a characteristic into the variety. The term "backcrossing" as used herein refers to the repeated crossing of a hybrid progeny back to the recurrent parent, e.g., backcrossing 1, 2, 3, 4, 5, 6, 7, 8, or more times to the recurrent parent. The parental rose plant that contributes the gene for the desired characteristic is termed the nonrecurrent or donor parent. This terminology refers to the fact that the nonrecurrent parent is used one time in the backcross protocol and therefore does not recur. The parental rose plant to which the gene or genes from the nonrecurrent parent are transferred is known as the recurrent parent as it is used for several rounds in the backcrossing protocol. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a rose plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. Often the goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; a common purpose is to add some commercially important trait or traits to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Many single gene traits have been identified that are not regularly selected for in the development of a new variety but that can be improved by backcrossing techniques. These single gene traits are well-known in the art.

Backcross Conversions of 'MEIBENBINO'

A backcross conversion of 'MEIBENBINO' occurs when DNA sequences are introduced through backcrossing with 'MEIBENBINO' utilized as the recurrent parent. Both naturally occurring DNA sequences and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. It has been demonstrated in the art that a backcross conversion can be made in as few as two backcrosses.

The complexity of the backcross conversion method depends on the type of trait being transferred (e.g., single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. Desired traits that may be transferred through backcross conversion include, but are not limited to, sterility (nuclear and cytoplasmic), fertility restoration, drought tolerance, nitrogen utilization, ornamental features, disease resistance (bacterial, fungal, or viral), insect resistance, and herbicide resistance. In addition, an introgression site itself, such as an FRT site, Lox site, or other site specific integration site, may be inserted by backcrossing and utilized for direct insertion of one or more genes of interest into a specific plant variety. In some embodiments, the number of loci that may be backcrossed into 'MEIBENBINO' is at least 1, 2, 3, 4, or 5, and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest may be accomplished by direct selection for a trait associated with a dominant allele. Transgenes or genes transferred via backcrossing typically function as a dominant single gene trait and are relatively easy to classify. Selection of progeny for a trait that is transferred via a recessive allele typically requires growing and selfing the first backcross generation to determine which plants carry the recessive alleles. Recessive traits may require additional progeny testing in successive backcross generations to determine the presence of the locus of interest. The last backcross generation may be selfed to give pure breeding progeny for the gene(s) being transferred, although a backcross conversion with a stably introgressed trait may also be maintained by further backcrossing to the recurrent parent with selection for the converted trait.

In addition, the above process and other similar processes described herein may be used to produce first generation progeny rose seed by adding a step at the end of the process that comprises crossing 'MEIBENBINO' with the introgressed trait or locus with a different plant and harvesting the resultant first generation progeny seed.

Molecular Techniques Using 'MEIBENBINO'

Molecular biological techniques have allowed the isolation and characterization of genetic elements with specific functions. Traditional plant breeding has principally been the source of new germplasm; however, advances in molecular technologies have allowed breeders to provide varieties with novel and desired commercial attributes. Molecular techniques such as transformation are popular in breeding ornamental plants and well-known in the art. See e.g., Vainstein, *Breeding for Ornamentals: Classical and Molecular Approaches*, KLUWER ACADEMIC PUBLISHERS (2002).

Breeding with Molecular Markers

Molecular markers may also be used during the breeding process for the selection of qualitative traits. For example, markers closely linked to alleles or markers containing sequences within the actual alleles of interest may be used to select plants that contain the alleles of interest during a backcrossing breeding program. The markers may also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses. Molecular markers, which include, but are not limited to, markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing 'MEIBENBINO'. See, e.g., Vainstein, *Breeding for Ornamentals: Classical and Molecular Approaches*, KLUWER ACADEMIC PUBLISHERS (2002).

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. See, e.g., Fletcher, et al., *QTL analysis of root morphology, flowering time, and yield reveals trade-offs in response to drought in Brassica napus* (2014) JOURNAL OF EXPERIMENTAL BIOLOGY. 66 (1): 245-256. QTL markers may also be used during the breeding process for the selection of qualitative traits. For example, markers closely linked to alleles or markers containing sequences within the actual alleles of interest can be used to select plants that contain the alleles of interest during a backcrossing breeding program.

Production of Double Haploids

The production of double haploids can also be used for the development of plants with a homozygous phenotype in the breeding program. For example, a rose plant for which 'MEIBENBINO' is a parent can be used to produce double haploid plants. Double haploids are produced by the doubling of a set of chromosomes (1 N) from a heterozygous plant to produce a completely homozygous individual. This can be advantageous because the process omits the generations of selfing needed to obtain a homozygous plant from a heterozygous source. See, e.g., Aswath, et al. *Haploid and Double Haploids in Ornamentals—A Review*, (2018) INT. J. CURR. MICROBIOL. APP. SCI. 7(7):1322-1336; and Ferrie, et al., *Review of Doubled Haploidy Methodologies in Ornamental Species* (2011) PROPAGATION OF ORNAMENTAL PLANTS. 11 (2): 63-77.

Thus, an embodiment is a process for making a substantially homozygous rose 'MEIBENBINO' progeny plant by producing or obtaining a seed from the cross of 'MEIBENBINO' and another rose plant and applying double haploid methods to the $F_1$ seed or $F_1$ plant or to any successive filial generation.

In particular, an embodiment is a process of making seed retaining the molecular marker profile of 'MEIBENBINO', such process comprising obtaining or producing $F_1$ seed for which 'MEIBENBINO' is a parent, inducing doubled haploids to create progeny without the occurrence of meiotic segregation, obtaining the molecular marker profile of 'MEIBENBINO', and selecting progeny that retain the molecular marker profile of 'MEIBENBINO'.

Signal Sequences for Targeting Proteins to Subcellular Compartments

Transport of a protein produced by a transgene to a sub cellular compartment, such as the chloroplast, vacuole, peroxisome, glyoxysome, cell wall, or mitochondrion, or for secretion into the apoplast, may be accomplished by means of operably linking a nucleotide sequence encoding a signal sequence (targeting sequence) typically to the 5' and/or 3' region of the transgene encoding the protein of interest. Signal sequences are well-known in the art. See, e.g., Becker, et al., PLANT MOL. BIOL., 20:49 (1992); Knox, et al., PLANT MOL. BIOL., 9:3-17 (1987); Lerner, et al., PLANT PHYSIOL., 91:124-129 (1989); Frontes, et al., PLANT CELL, 3:483-496 (1991); Matsuoka, et al., PROC. NATL. ACAD. SCI., 88:834 (1991); Gould, et al., J. CELL. BIOL., 108:1657 (1989); Creissen, et al., PLANT J., 2:129 (1991); Kalderon, et al., CELL, 39:499-509 (1984); and Steifel, et al., PLANT CELL, 2:785-793 (1990).

Gene Silencing

Techniques for gene silencing are well-known in the art, including, but not limited to, knock-outs (such as by insertion of a transposable element such as Mu) or other genetic elements such as a FRT, Lox, or other site specific integration sites; antisense technology; co-suppression; RNA interference; virus-induced gene silencing; target-RNA-specific ribozymes; hairpin structures; MicroRNA; ribozymes; oligonucleotide mediated targeted modification; Zn-finger targeted molecules; CRISPR/Cas9 system; and other methods or combinations of the above methods known to those of skill in the art. See, e.g., Sheehy, et al., PNAS USA, 85:8805-8809 (1988); U.S. Pat. Nos. 5,107,065; 5,453,566; 5,759,829; Jorgensen, TRENDS BIOTECH., 8(12):340-344 (1990); Flavell, PNAS USA, 91:3490-3496 (1994); Neuhuber, et al., MOL. GEN. GENET., 244:230-241 (1994); Napoli, et al., PLANT CELL, 2:279-289 (1990); U.S. Pat. No. 5,034,323; Sharp, GENES DEV., 13:139-141 (1999); Zamore, et al., CELL, 101:25-33 (2000); Montgomery, et al., PNAS USA, 95:15502-15507 (1998); Burton, et al., PLANT CELL, 12:691-705 (2000); Baulcombe, CURR. OP. PLANT BIO., 2:109-113 (1999); Haseloff, et al., NATURE, 334:585-591 (1988); Smith, et al., NATURE, 407:319-320 (2000); U.S. Pat. Nos. 6,423, 885; 7,138,565; 6,753,139; 7,713,715; Aukerman & Sakai, PLANT CELL, 15:2730-2741 (2003); Steinecke, et al., EMBO J., 11:1525 (1992); Perriman, et al., ANTISENSE RES. DEV., 3:253 (1993); U.S. Pat. Nos. 6,528,700; 6,911,575; 7,151,201; 6,453,242; 6,785,613; 7,177,766; 7,788,044; International Publication No. WO2014/068346; Martinelli, et al., *Proposal of a Genome Editing System for Genetic Resistance to Tomato Spotted Wilt Virus* 2014 AMERICAN JOURNAL OF APPLIED SCIENCES; Noman, et al., *CRISPR-Cas9: Tool for Qualitative and Quantitative Plant Genome Editing*, November 2016 FRONTIERS IN PLANT SCIENCE Vol. 7; and Zhang et al., *Exploiting the CRISPR/Cas9 System for Targeted Genome Mutagenesis in Petunia* February 2016 SCIENCE REPORTS Volume 6.

Tissue Culture

Further reproduction of the variety can occur by tissue culture and regeneration. Tissue culture (cell culture) of various tissues of ornamental plants; 'MEIBENBINO' and regeneration of plants therefrom are well-known and widely published. See, e.g., Rego, et al., CROP BREEDING AND APPLIED TECHNOLOGY. 1(3): 283-300 (2001); Komatsuda, et al., CROP SCI., 31:333-337 (1991); Stephens, et al., THEOR. APPL. GENET., 82:633-635 (1991); Komatsuda, et al., PLANT CELL, TISSUE AND ORGAN CULTURE, 28:103-113 (1992); Dhir, et al., PLANT CELL REPORTS, 11:285-289 (1992); and Shetty, et al., PLANT SCIENCE, 81:245-251 (1992). Thus, another embodiment is to provide cells which upon growth and differentiation produce rose plants having the physiological and morphological characteristics of 'MEIBENBINO' described in the present application.

Regeneration refers to the development of a plant from tissue culture or cell culture. Exemplary types of tissue cultures or cell cultures are protoplasts, calli, plant clumps, and plant cells that can generate tissue culture that are intact in plants or parts of plants, such as pollen, ovules, embryos, protoplasts, meristematic cells, callus, pollen, leaves, ovules, anthers, cotyledons, hypocotyl, pistils, roots, root tips, flowers, seeds, petiole, shoot, or stems, and the like. Means for preparing and maintaining plant tissue culture and plant cell cultures are well-known in the art.

While a number of exemplary aspects and embodiments have been disclosed above, those of skill in the art will recognize certain modifications, permutations, additions, and sub-combinations thereof. The foregoing discussion of the embodiments has been presented for purposes of illustration and description. The foregoing is not intended to limit the embodiments to the form or forms disclosed herein.

Moreover, though the description of the embodiments has included description of one or more embodiments and certain variations and modifications, other variations and modifications are within the scope of the embodiments (e.g., may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

EXAMPLES

Prophetic Example 1: A Non-Red Colored Flower Rose Plant Produced by Cultivating a Spontaneous Mutation of a Rose Plant of Variety 'MEIBENBINO'

A 'MEIBENBINO' rose plant is found to have a spontaneous mutation wherein a single flower on the plant is a different color than the rest of the red colored flowers on the plant. The single non-red colored flower is selected, cut, and propagated as a single plant. This spontaneous mutation plant grown from the single non-red colored flower is found to exhibit all flowers to be the same color as the single non-red colored flower. All other characteristics of the new spontaneous mutation plant variety are found to be the same as 'MEIBENBINO'. This new spontaneous mutation plant is then asexually produced by a number of routes, including budding, grafting, and the use of cuttings. Asexual propagation by the above-mentioned techniques will show that the characteristics of the new spontaneous mutation plant variety are stable and are strictly transmissible by such asexual propagation from one generation to another. Accordingly, the new spontaneous mutation variety will undergo asexual propagation in a true-to-type manner.

Prophetic Example 2: A Double Rose Plant Produced by Cultivating a Spontaneous Mutation of a Rose Plant of Variety 'MEIBENBINO'

A 'MEIBENBINO' rose plant is found to have a spontaneous mutation wherein a single flower on the plant has an increased number of petals compared to the rest of the flowers on the plant; the single flower on the plant is a double rose flower. The double flower is selected, cut, and propagated as a single plant. This spontaneous mutation plant grown from the double flower is found to exhibit all flowers that are double flowers with the higher petal count. All other characteristics of the new spontaneous mutation plant variety are found to be the same as 'MEIBENBINO'. This new spontaneous mutation plant is then asexually produced by a number of routes, including budding, grafting, and the use of cuttings. Asexual propagation by the above-mentioned techniques will show that the characteristics of the new spontaneous mutation plant variety are stable and are strictly transmissible by such asexual propagation from one generation to another. Accordingly, the new spontaneous mutation variety will undergo asexual propagation in a true-to-type manner.

Prophetic Example 3: A Ground Cover Rose Plant Produced by Cultivating a Spontaneous Mutation of a Rose Plant of Variety 'MEIBENBINO'

A single asexually produced progeny plant of 'MEIBENBINO' is found to have a ground cover habit instead of the semi-erect habit of 'MEIBENBINO'. All other characteristics of this new spontaneous mutation plant variety are found to be the same as 'MEIBENBINO'. This new spontaneous mutation ground cover habit plant is selected and asexually reproduced by a number of routes, including budding, grafting, and the use of cuttings. Asexual propagation by the above-mentioned techniques will show that the characteristics of the new spontaneous mutation plant variety are stable and are strictly transmissible by such asexual propagation from one generation to another. As such, all asexually reproduced plants from the spontaneous mutation ground cover habit plant will have ground cover habit. Accordingly, the new spontaneous mutation variety will undergo asexual propagation in a true-to-type manner.

Prophetic Example 4: A Rose Plant Produced by Cultivating a Mutated Plant of a Rose Plant of Variety 'MEIBENBINO'

A 'MEIBENBINO' plant or plant part thereof is exposed to whole genome mutagenesis conditions, such as temperature, long-term seed storage, tissue culture conditions, ionizing radiation, and/or chemical mutagens. Then the mutated plant lines or seeds are screened for a desired trait, such as non-red flower color, increased petal count, increased cold hardiness, different growth habit, or increased resistance to an herbicide, insecticide, or disease. Once the desired trait is observed in one or more mutated plants, those individual plants are selected and may be backcrossed using 'MEIBENBINO'. Then the mutated plant or the resulting backcrossed mutated plant is asexually reproduced by a number of routes, including budding, grafting, and the use of cuttings. Asexual propagation by the above-mentioned techniques will show that the characteristics of the new mutation plant variety are stable and are strictly transmissible by such asexual propagation from one generation to another. As such, all asexually reproduced plants will have the desired trait(s) and the remaining non-mutated traits of 'MEIBENBINO'.

Prophetic Example 5: A Rose Plant Produced by Cultivating a Mutated Plant of a Rose Plant of Variety 'MEIBENBINO'

A 'MEIBENBINO' plant or plant part thereof is exposed to targeted mutagenesis intended to edit or change a particular gene or genomic region, such targeted mutagenesis include targeting induced local lesions in genomes, zinc finger nuclease mediated mutagenesis, CRISPR/Cas9, meganucleases, and/or gene editing. Then the mutated plant lines or seeds are screened for a desired trait, such as non-red flower color, increased petal count, increased cold hardiness, different growth habit, or increased resistance to an herbicide, insecticide, or disease. Once the desired trait is observed in one or more mutated plants, those individual plants are selected and may be backcrossed using 'MEIBENBINO'. Then the mutated plant or the resulting backcrossed mutated plant is asexually reproduced by a number of routes, including budding, grafting, and the use of cuttings. Asexual propagation by the above-mentioned techniques will show that the characteristics of the new mutation plant variety are stable and are strictly transmissible by such asexual propagation from one generation to another. As such, all asexually reproduced plants will have the desired trait(s) and the remaining non-mutated traits of 'MEIBENBINO'.

Prophetic Example 6: A Rose Plant Produced by Transforming a Plant of a Rose Plant of Variety 'MEIBENBINO'

A rose plant of variety 'MEIBENBINO' is transformed with a transgene thereby creating a new transgenic rose plant or plant parts containing the genetic material of one or more genes or transgenes. The genetic material of one or more genes or transgene confers a desired trait, such as resistance to an herbicide, insecticide, or disease. Thus, the transgenic rose plant will have the desired trait. Once the desired trait is observed in one or more transgenic plants, those individual transgenic plants are selected and may be backcrossed using 'MEIBENBINO'. Then the transgenic plant or the resulting backcrossed transgenic plant is asexually reproduced by a number of routes, including budding, grafting, and the use of cuttings. Asexual propagation by the above-mentioned techniques will show that the characteristics of the new mutation plant variety are stable and are strictly transmissible by such asexual propagation from one generation to another. As such, all asexually reproduced plants will have the desired trait(s) and the remaining non-mutated traits of 'MEIBENBINO'. As such, the transgenic rose plant may be an herbicide, insecticide, or disease resistant plant and contain the other characteristics of 'MEIBENBINO'.

Prophetic Example 7: A Lavender Colored Double Flower Rose Plant Produced by Crossing a Plant of Variety 'MEIBENBINO' with a Plant of Variety APPLAUSE™

A rose plant variety that exhibits lavender colored double flowers is created by artificial pollination wherein two parents will be crossed which previously had been studied in the hope that they will contribute the desired characteristics. The female parent (i.e., the seed parent) is the 'MEIBENBINO' variety. The male parent (i.e., the pollen parent) is the APPLAUSE™ variety.

The parentage of the new variety can be summarized as follows:

'MEIBENBINO' x APPLAUSE™

The seeds resulting from the above pollination will be sown and small plants will be obtained which will be physically and biologically different from each other. Selective study will result in the identification of a single plant of a new variety of rose plant that will possess the following combination of characteristics:

(a) very abundantly and nearly continuously forms attractive lavender colored double flowers, (b) forms attractive, very dense, glossy foliage, (c) exhibits very good tolerance to diseases, particularly against Black Spot, and (d) is well suited for providing attractive ornamentation.

All characteristics of the new plant variety are found to be the same as 'MEIBENBINO' with the exception of the flower color (lavender vs. red) and number of petals (double vs. single).

Prophetic Example 8: A Double Flower Fragrant Rose Plant Produced by Crossing a Plant of Variety 'MEIBENBINO' with a Plant of Variety 'DOLLY PARTON' (U.S. Plant patent Ser. No. 5,608)

A rose plant variety that exhibits double flowers with a high petal count and produces outstanding fragrance is created by artificial pollination wherein two parents will be crossed which previously had been studied in the hope that they will contribute the desired characteristics. The female parent (i.e., the seed parent) is the 'MEIBENBINO' variety. The male parent (i.e., the pollen parent) is the 'DOLLY PARTON' variety.

The parentage of the new variety can be summarized as follows:

'MEIBENBINO' x 'DOLLY PARTON'

The seeds resulting from the above pollination will be sown and small plants will be obtained which will be physically and biologically different from each other. Selective study will result in the identification of a single plant of a new variety of rose plant that will possess the following combination of characteristics:

(a) very abundantly and nearly continuously forms attractive double flowers with a high petal count and produces outstanding fragrance, which is heady and somewhat fruity, (b) forms attractive, very dense, glossy foliage,
(c) exhibits very good tolerance to diseases, particularly against Black Spot, and
(d) is well suited for providing attractive ornamentation.

All characteristics of the new plant variety are found to be the same as 'MEIBENBINO' with the exception of the petal count (double flowers with about 35 or more petals vs. single flowers with about 9-12 petals) and the fragrance (outstanding which is heady and somewhat fruity vs. no fragrance).

Prophetic Example 9: A Cold Hardiness Rose Plant with Salmon Colored Flowers Produced by Crossing a Plant of Variety 'MEIBENBINO' with a Plant of Variety 'FARROWRSP' (U.S. Plant patent Ser. No. 30,383)

A rose plant variety that exhibits cold hardiness and produces salmon colored flowers is created by artificial pollination wherein two parents will be crossed which previously had been studied in the hope that they will contribute the desired characteristics. The female parent (i.e., the seed parent) is the 'MEIBENBINO' variety. The male parent (i.e., the pollen parent) is the 'FARROWRSP' variety.

The parentage of the new variety can be summarized as follows:
'MEIBENBINO' x 'FARROWRSP'

The seeds resulting from the above pollination will be sown and small plants will be obtained which will be physically and biologically different from each other. Selective study will result in the identification of a single plant of a new variety of rose plant that will possess the following combination of characteristics:

(a) very abundantly and nearly continuously forms attractive salmon-colored blossoms,
(b) forms attractive, very dense, glossy foliage,
(c) exhibits very good tolerance to diseases, particularly against Black Spot, and very good cold hardiness, and
(d) is well suited for providing attractive ornamentation.

All characteristics of the new plant variety are found to be the same as 'MEIBENBINO' with the exception of cold hardiness (hardy to Zone 3 vs. hardy to Zone 4-10) and flower color (salmon vs. red).

Prophetic Example 10: A Ground Coverage Rose Plant Produced by Crossing a Plant of Variety 'MEIBENBINO' with a Plant of Variety 'Meigalpio' (U.S. Plant patent Ser. No. 17,877)

A rose plant variety that exhibits ground coverage growth habit and provides a higher number of flowers per stem is created by artificial pollination wherein two parents will be crossed which previously had been studied in the hope that they will contribute the desired characteristics. The female parent (i.e., the seed parent) is the 'MEIBENBINO' variety. The male parent (i.e., the pollen parent) is the 'Meigalpio' variety.

The parentage of the new variety can be summarized as follows:
'MEIBENBINO' x 'Meigalpio'

The seeds resulting from the above pollination will be sown and small plants will be obtained which will be physically and biologically different from each other. Selective study will result in the identification of a single plant of a new variety of rose plant that will possess the following combination of characteristics:

(a) very abundantly and nearly continuously forms attractive red colored blossoms,
(b) forms attractive, very dense, glossy foliage,
(c) exhibits very good tolerance to diseases, particularly against Black Spot,
(d) displays a ground coverage habit, and
(e) is well suited for providing attractive ornamentation.

All characteristics of the new plant variety are found to be the same as 'MEIBENBINO' with the exception of growth habit (ground coverage habit vs. bush) and higher number of flowers per stem (about 6-15 flowers per stem vs. about 1-6 flowers per stem).

Prophetic Example 11: A Pink Colored Flower Climbing Rose Plant Produced by Crossing a Plant of Variety 'MEIBENBINO' with a Plant of Variety 'Meiviowit' (U.S. Plant patent Ser. No. 16,739)

A rose plant variety that exhibits pink colored flowers and a climbing growth habit is created by artificial pollination wherein two parents will be crossed which previously had been studied in the hope that they will contribute the desired characteristics. The female parent (i.e., the seed parent) is the 'MEIBENBINO' variety. The male parent (i.e., the pollen parent) is the 'Meiviowit' variety.

The parentage of the new variety can be summarized as follows:
'MEIBENBINO' x 'Meiviowit'

The seeds resulting from the above pollination will be sown and small plants will be obtained which will be physically and biologically different from each other. Selective study will result in the identification of a single plant of a new variety of rose plant that will possess the following combination of characteristics:

(a) very abundantly and nearly continuously forms attractive pink colored flowers,
(b) forms attractive, very dense, glossy foliage,
(c) exhibits very good tolerance to diseases, particularly against Black Spot,
(d) displays a climbing habit, and
(e) is well suited for providing attractive ornamentation.

All characteristics of the new plant variety are found to be the same as 'MEIBENBINO' with the exception of the petal count (climbing habit vs. bush) and flower color (pink vs. red).

Prophetic Example 12: A Double Flower Rose Plant Produced by Crossing a First Plant of Variety 'MEIBENBINO' with a Second Plant of Variety 'MEIBENBINO'

A rose plant variety that exhibits double flowers and very good resistance to disease is created by artificial pollination wherein two parents will be crossed which previously had been studied in the hope that they will contribute the desired characteristics. The female parent (i.e., the seed parent) is the 'MEIBENBINO' variety. The male parent (i.e., the pollen parent) is the 'MEIBENBINO' variety.

The parentage of the new variety can be summarized as follows:
'MEIBENBINO' x 'MEIBENBINO'

The seeds resulting from the above pollination will be sown and small plants will be obtained which will be physically and biologically different from each other. Selective study will result in the identification of a single plant of a new variety of rose plant that will possess the following combination of characteristics:

(a) very abundantly and nearly continuously forms attractive red colored double flowers,
(b) forms attractive, very dense, glossy foliage,
(c) exhibits very good tolerance to diseases, particularly against Black Spot, and
(d) is well suited for providing attractive ornamentation.

All characteristics of the new plant variety are found to be the same as 'MEIBENBINO' with the exception of the petal count (double flowers with about 23 petals vs. single flowers with 9-12 petals) and plant size (plant height of 1.0 m vs. 35 cm).

DEPOSIT INFORMATION

Under the provisions of the Budapest Treaty on the International Recognition of the Deposit of Microorganisms for the Purpose of Patent Procedure, Applicant has deposited biological material comprising 'MEIBENBINO' plant tissue disclosed herein with the International Depositary Authority of Provasoli-Guillard National Center for Marine Algae and Microbiota (NCMA) at Bigelow Laboratory for Ocean Science (6 Bigelow Drive, East Boothbay, ME 04544), on Jan. 6, 2021 under NCMA Accession number 202101001.

I claim:

1. A rose plant that is an F1 of variety 'MEIBENBINO', produced by a process comprising:
    a) crossing a first plant with a second plant,
    b) harvesting progeny seed or embryo of a), and
    c) cultivating the harvested progeny seed or embryo;
    wherein said first plant is a rose plant of variety 'MEIBENBINO', and
    wherein a representative sample of plant tissue of said variety 'MEIBENBINO' has been deposited under NCMA Accession Number 202101001.

2. The rose plant of claim 1, wherein said second plant is a rose plant of variety 'MEIBENBINO'.

3. The rose plant of claim 1, wherein said second plant is a plant of a different variety.

4. The rose plant of claim 1, wherein the rose plant has one or more desired trait of variety 'MEIBENBINO'.

5. The rose plant of claim 4, wherein the rose plant is a miniature rose plant, exhibits good tolerance to disease, nearly continuously forms blossoms, and forms dense, glossy foliage.

* * * * *